United States Patent [19]

Buckberg et al.

[11] Patent Number: 4,944,729
[45] Date of Patent: Jul. 31, 1990

[54] FEMORAL ARTERIAL CANNULA

[75] Inventors: Gerald D. Buckberg; James V. Maloney, Jr., both of Los Angeles; Kenneth A. Jones, Lake Elsinore; Weldon D. West, Mission Viejo, all of Calif.

[73] Assignee: Shiley, Inc., Irvine, Calif.

[21] Appl. No.: 238,154

[22] Filed: Aug. 29, 1988

[51] Int. Cl.$^5$ .............................................. A61M 5/00
[52] U.S. Cl. ................................ 604/164; 604/165; 604/264; 604/280
[58] Field of Search ................ 604/93, 164, 165, 167, 604/170, 177, 280, 264, 117

[56] References Cited

U.S. PATENT DOCUMENTS

| | | | |
|---|---|---|---|
| 3,776,239 | 12/1973 | Cooley | 604/117 |
| 4,194,504 | 3/1980 | Harms et al. | 604/117 |
| 4,417,886 | 11/1983 | Frankhouser et al. | 604/164 |
| 4,650,473 | 3/1987 | Bartholomew et al. | 604/177 |
| 4,781,692 | 11/1988 | Jagger et al. | 604/164 |
| 4,804,365 | 2/1989 | Litzkie et al. | 604/280 |

*Primary Examiner*—Stephen C. Pellegrino
*Attorney, Agent, or Firm*—Knobbe, Martens, Olson & Bear

[57] ABSTRACT

An arterial cannula is formed with an angled shoulder that limits the degree of insertion of cannula tip into an artery. The shoulder also forms a seal with the artery. Suture flaps are formed on the cannula to attach the cannula to the patient's skin. A stylet for the cannula has a stop on its exterior that prevents blood flow between the cannula and the stylet, and permits clamping of the cannula with the stylet partially withdrawn. A removable anti-backflow ring seals the cannula and provides a convenient initial movement limit for the stylet stop.

12 Claims, 2 Drawing Sheets

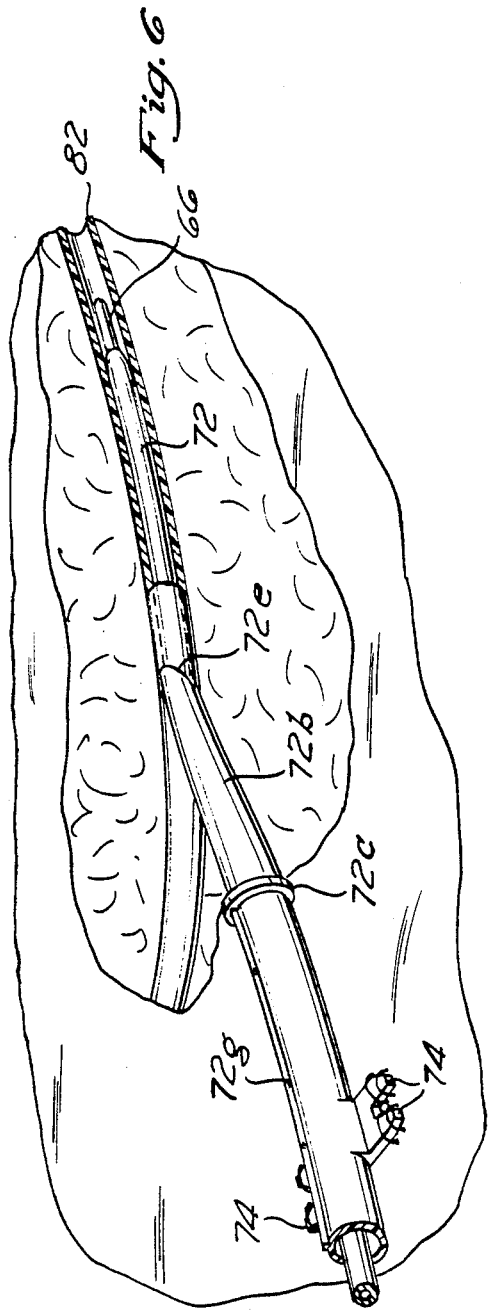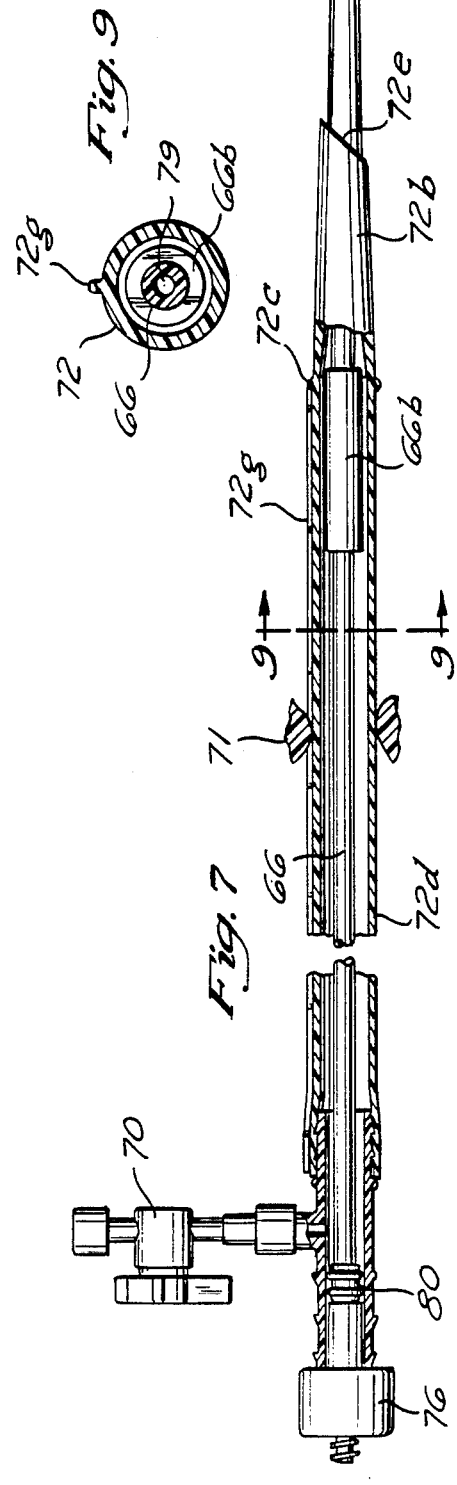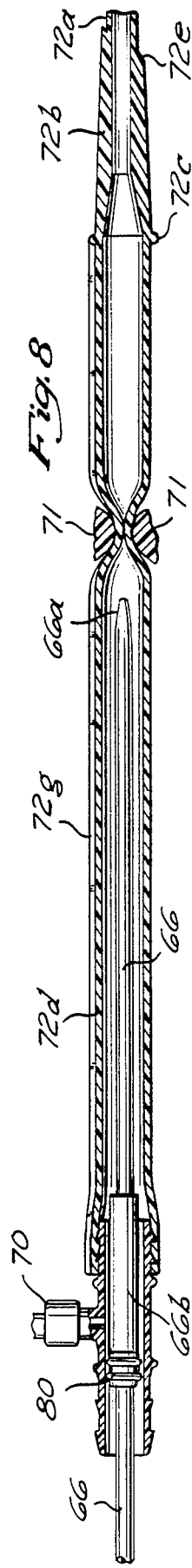

FEMORAL ARTERIAL CANNULA

FIELD OF THE INVENTION

This invention relates to an improved cannula or catheter assembly particularly useful in medical operations.

BACKGROUND OF THE INVENTION

In recent years, there has been developed a femoral-to-femoral cardiopulmonary bypass system wherein it is not necessary to open the patient's chest. Such a system has many obvious advantages and is useful in situations where medical treatment can be administered to the heart without having open-chest surgery. To accomplish this, it is necessary to employ large diameter cannulas and catheters in order to maximize blood flow. It is also, of course, important that the necessary connections to the cannulas be made with a minimum of blood loss, in a minimum of time, and with a minimum of trauma and risk to the patient. Cannulating a femoral artery is particularly difficult because of the pressure involved as well as the large flow through the artery. Accordingly, there is a need for improvements in such devices.

SUMMARY OF THE INVENTION

Briefly stated, the cannula of the present invention comprises an elongated tube having a tip section adapted to be inserted into a vascular conduit such as a patient's artery. A shoulder is formed on the exterior of the tube adjacent the tip section to limit the insertion of the tip section into the artery. The surface of the shoulder that engages the artery is formed at an angle consistent with the angle at which the cannula is inserted, whereby the artery surrounding the insertion point generally conforms to the shoulder such that a seal is formed.

As another feature of the cannula, suture flaps are provided on the exterior of the cannula for use in securing the cannula to the patient's skin after the cannula has been inserted. With that arrangement, the proximal end of the cannula can be manipulated considerably while making connections to other apparatus, such as a pump or an oxygenator, without disturbing the distal end of the cannula.

A stylet for the cannula includes a stop on its outer periphery which slides within the cannula. When the stylet is ready to be withdrawn, it is retracted an initial amount to a point where the stop engages an anti-backflow ring. A clamp is then placed on the cannula at a location between the tip of the partially-withdrawn stylet and the patient. Blood flow from the patient is thus prevented by the clamp, and the stylet may be safely withdrawn. The anti-backflow ring is positioned in the proximal end of the cannula or a fitting connected to the cannula and provides a seal between the stylet and the cannula so that there is no blood leakage out of the cannula during the insertion and connecting procedures. As noted, the ring also temporarily prevents further withdrawal of the cannula. However, the stylet is completely withdrawn with increased force the ring is withdrawn with it so that the end of the cannula is ready to be connected to the bypass system.

BRIEF DESCRIPTION OF THE DRAWINGS

FIG. 6 is an enlarged perspective schematic view of the cannula assembly inserted in a femoral artery;

FIG. 7 is a side elevational, partially sectionalized view of the assembly of FIG. 3;

FIG. 8 is a cross-sectional view of the cannula assembly with the stylet partially withdrawn and with the cannula clamped to prevent flow therethrough;

FIG. 9 is a cross-sectional view on line 9—9 of FIG. 7.

DETAILED DESCRIPTION OF THE PREFERRED EMBODIMENT

Figure 3:
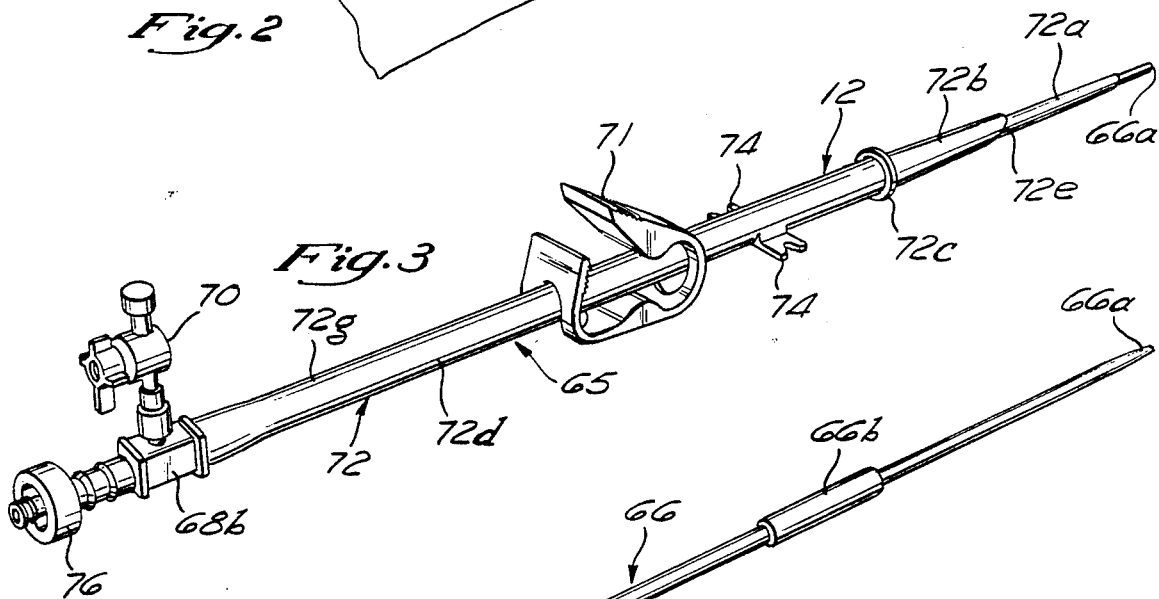
FIG. 3 is a perspective view of the cannula assembly of FIGS. 1 and 2.

A femoral arterial cannula assembly 65 is shown in FIG. 3. The assembly includes a cannula 64, a stylet 66 which is slidably received within the cannula, a fitting 68 secured to the proximal end of the cannula, a stopcock 70 on the fitting, and a clamp 71.

The cannula 64 comprises an elongated tubular body 72 preferably made from a medical-grade polyvinyl chloride, or silicone rubber. The body 72 has three primary sections including a distal tip section 72a for insertion into the femoral artery, an intermediate section 72b adapted to extend from the artery to a raised suture stabilizing ring 72c to be located near the exterior skin of the leg, and an exterior section 72d extending from the suture ring 72c to the fitting 68.

The tip of section 72a is tapered to facilitate insertion into an artery. In a preproduction version of the cannula, the exterior diameter of the tip section 72a is 6.68 mm or 20 French, and the interior diameter is 5.08 mm. The intravascular length of the tip section 72a in a preproduction version is 5.88 cm, which is a desirable length to ensure adequate seating within the artery.

The intermediate section 72b has a length of about 5 cm, with an interior diameter that tapers to about 9.27 mm, and with an exterior diameter which tapers from the tip end of about 8.4 mm and increases to about 12–13 cm. Thus, it can be seen that there is a significant exterior diameter change from the tip section 72a to the tip end of the intermediate section 72b. This diameter change forms an annular shoulder 72e adapted to engage the exterior of an artery. That shoulder is formed at an angle of approximately 45° with respect to a diametrical plane through the cannula. It has been found that this angle is particularly desirable for sealing with the exterior of the femoral artery when the cannula is inserted in the direction towards the heart.

Due to the angled shoulder and the angle at which the cannula tip is inserted in the femoral artery, it is important the cannula be rotationally oriented properly. Thus, for orientation purposes, there is formed an elongated orientation rib 72g on the exterior of sections 72b and 72d extending from the suture ring 72c to the proximal end of the body which mates with the fitting 68. The section 72d is about 19 cm in length, making the overall length of the cannula about 33 cm. The interior and exterior diameters are constant with the end of section 72b.

A pair of suture wings or flaps 74 are formed integral with and extend outwardly from the cannula exterior section 72d. The flaps form a lower surface which is approximately tangent with the exterior of the section 72d. The suture wings in a prototype are positioned about 5 cm from the suture ring 72c.

Figure 4:
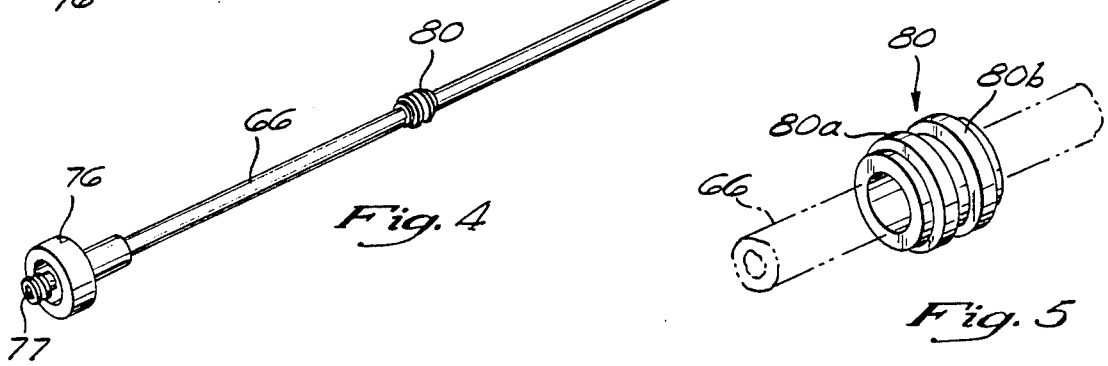
FIG. 4 is a perspective view of the stylet of the assembly of FIG. 3.
Figure 5:
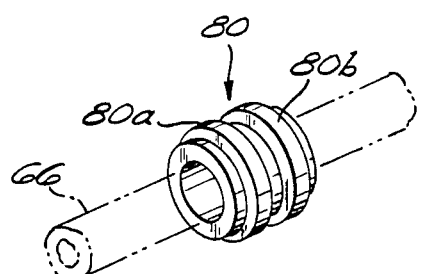
FIG. 5 is a perspective view of an anti-backflow ring of the cannula assembly.

Referring to FIGS. 3 and 4, the stylet 66 is an elongated flexible tubular element preferably made of medical-grade polyvinyl chloride or silicone rubber. The stylet 66 is slightly longer than the cannula 12 having a tapered tip 66a on one end which extends beyond the tip of the cannula when the stylet is fully inserted therein. The overall length is about 42 cm. A knob 76 on the other end of the stylet extends beyond the fitting 68 and is useful for installing and removing the stylet from the cannula. The diameter of the stylet is slightly smaller than the inner diameter of the tip of the cannula. A small diameter lumen 77 is formed throughout the length of the catheter and is adapted to receive a small diameter guidewire. Included on the stylet 66 is an elongated cylindrical stop or plug 66b having an exterior diameter which is sized to slide relatively easily within the cannula, but nevertheless there is resistance to movement caused by the plug 66b engaging the interior of the cannula. The plug 66b is spaced from the tip end of the stylet about 15 cm and has a length of about 4 cm. This means that the end of the plug 66b closest to the tip 66a of the stylet is located at the suture ring of the cannula when the stylet is fully inserted in the cannula, as seen in FIG. 7.

Also included in the cannula assembly is an anti-backflow ring 80 preferably made of medical-grade silicone rubber. The ring has a short barrel-like tubular shape with two axially spaced outwardly extending annular ribs 80a. The ribs are dimensioned such that the backflow ring fits fairly tightly within the interior of the fitting 68 or the cannula end; and in that position, fits snugly on the stylet 66.

Mounted on the exterior of the cannula between the suture wings and the fitting 68 is the adjustable medical clamp 71. The clamp is of standard construction, adapted to be manually set to pinch the cannula closed when the stylet is removed.

Figure 1:
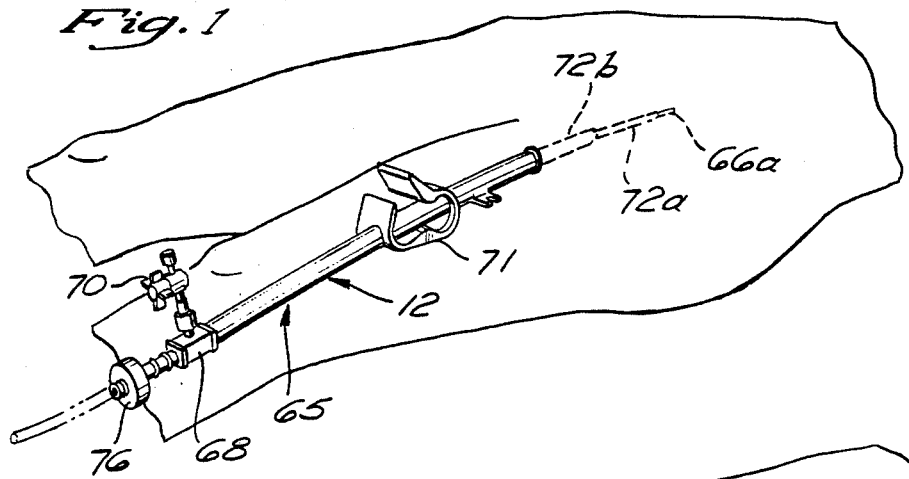
FIG. 1 is a schematic perspective view of an arterial cannula inserted in a femoral artery.

In use, the guidewire is inserted into the femoral artery followed by the cannula with the stylet fully inserted, as shown in FIGS. 1, 3 and 6. The cannula is preferably introduced by use of the Seldinger technique, or a cutdown procedure along with vessel dilation. The assembly, guided by the guidewire, is inserted to the point where the cannula angled shoulder 72e engages the exterior of an artery 82 with the cannula tip section 72a extending into the artery, together with the tip of the stylet, as illustrated in FIG. 6. It can be seen from that figure that the angled shoulder 72e seal engages the artery in a manner such that the artery substantially conforms to the shoulder with the exterior of the artery, and limits insertion. With the cannula so positioned, it is sutured to the leg by means of the wings, and the raised suture ridge, as shown in FIG. 6.

Figure 2:
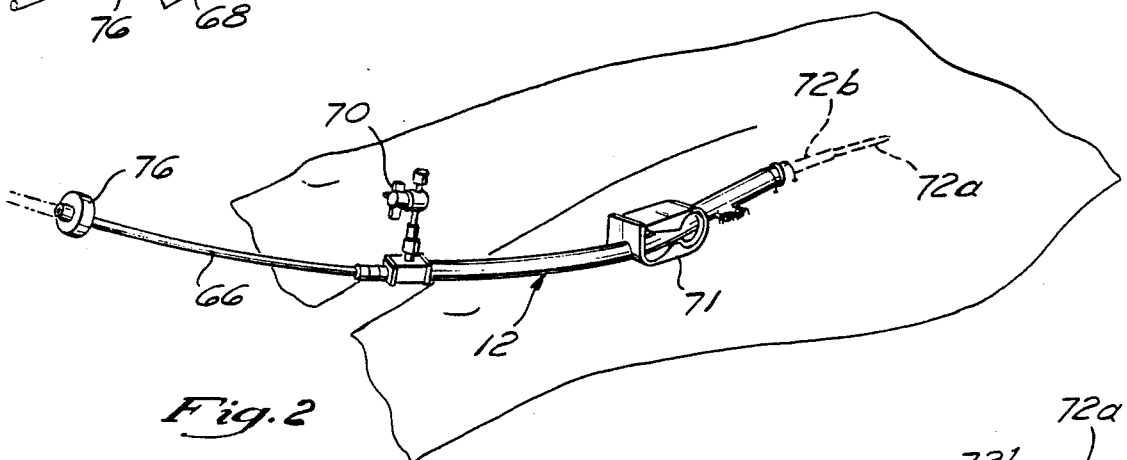
FIG. 2 is a view similar to FIG. 1, but with the stylet of the cannula assembly partially withdrawn.

With the cannula so positioned, there is little blood leakage through the hole in the artery as a result of the seal with the shoulder 72e. Also, the ring 80 prevents leakage through the annular passage between the stylet and the cannula, as seen in FIG. 7. With the forward portion of the cannula relatively firmly positioned on the patient's leg, the proximal end of the cannula is free to be raised or manipulated, as may be appreciated from FIG. 2.

When it is desirable to connect the cannula to an extracorporeal circuit, the stylet 66 is partially withdrawn by pulling on the knob 76 to the position shown in FIG. 8, wherein the plug 66b on the stylet engages anti-backflow ring 80 in the fitting. Note that there is firm resistance by the ring to withdrawing the ring 80 out of the cannula so that an operator recognizes the stopping point. The tip 66a of the stylet is spaced considerably from the suture ring since the length of the stylet from the plug 66b to its tip 66a is somewhat less than the length of the cannula from its fitting end to the suture ring 72c. With the stylet 66 so positioned, the clamp 71 is squeezed onto the cannula section 72d at a location between the tip 66a of the stylet and the suture ring 72c, as seen in FIG. 8. By locating the clamp close to the tip 66a of the stylet, there is only a small quantity of blood between the clamp and the ring 80. Once the clamp has been positioned and closed, the stylet can be withdrawn completely with a pulling force greater than that to move the stop, such that the ring 80 in the end of the fitting is also withdrawn, captured on the stylet 66. At this stage, there is only a small quantity of blood in the open end of the cannula, and it is not under pressure. Because of this and the suture wings, the proximal end of the cannula can be easily handled for making connections to a pump and priming the cannula without loss of blood.

We claim:

1. A cannula comprising:
    an elongated tube having a flexible tip section adapted to be inserted into a wall of a vascular conduit and extend generally parallel to the axis of said conduit; and
    a flexible intermediate section adjacent to said tip section having a diameter larger than that of the tip section whereby a shoulder is formed at the juncture of the two sections, said shoulder being sufficiently larger than the diameter of the conduit such that it engages the exterior of the conduit and limits the insertion of the tip section into the conduit, the surface of said shoulder for engaging the conduit substantially conforming to the exterior of the conduit consistent with the angle of insertion of the tip section into the conduit whereby a seal is formed by the shoulder with respect to the exterior of the conduit, said angle being an acute angle so as to facilitate the bending of the tube in insertion of said tip section into said conduit.

2. The cannula of claim 1, wherein the surface of said shoulder which engages the conduit is formed at an angle of approximately 45° with respect to the diameter of the cannula.

3. The cannula of claim 2, including an orientation indicator on the exterior of said cannula to indicate the desired circumferential orientation for the cannula when being inserted into the conduit.

4. A cannula comprising:
    an elongated tube having a tip section adapted to be inserted into a vascular conduit;
    an intermediate section adjacent to said tip section having a diameter larger than that of the tip section whereby a shoulder is formed at the juncture of the two sections, said shoulder being sufficiently larger than the diameter of the conduit such that it engages the exterior of the conduit and limits the insertion of the tip section into the conduit, the surface of said shoulder for engaging the conduit substantially conforming to the exterior of the conduit consistent with the angle of insertion of the tip section into the conduit, whereby a seal is formed by the shoulder with respect to the exterior of the conduit; and a suture ring on the exterior of the cannula spaced from said shoulder on the side of the shoulder opposite from said tip section.

5. A cannula comprising:

an elongated tube having a tip section adapted to be inserted into a vascular conduit;

an intermediate section adjacent to said tip section having a diameter larger than that of the tip section whereby a shoulder is formed at the juncture of the two sections, said shoulder being sufficiently larger than the diameter of the conduit such that if engages the exterior of the conduit and limits the insertion of the tip section into the conduit, the surface of said shoulder for engaging the conduit substantially conforming to the exterior of the conduit consistent with the angle of insertion of the tip section into the conduit, whereby a seal is formed by the shoulder with respect to the exterior of the conduit; and a pair of suture wings extending outwardly from the exterior of the cannula adapted to be sutured to a patient's skin so as to maintain the cannula tip section properly in the conduit while leaving the end of the cannula outwardly from the wings to be easily manipulated.

6. A cannula assembly comprising:

an elongated tube having a tip section adapted to be inserted into a vascular conduit;

an intermediate section adjacent to said tip section having a diameter larger than that of the tip section whereby a shoulder is formed at the juncture of the two sections, said shoulder being sufficiently larger than the diameter of the conduit such that it engages the exterior of the conduit and limits the insertion of the tip section into the conduit, the surface of said shoulder for engaging the conduit substantially conforming to the exterior of the conduit consistent with the angle of insertion of the tip section into the conduit, whereby a seal is formed by the shoulder with respect to the exterior of the conduit; and a stylet adapted to fit within the cannula, said stylet including a plug on its exterior which slides within the cannula and temporarily limits withdrawal of the stylet.

7. The cannula of claim 6, including an anti-backflow ring positioned in the proximal end of the cannula and extending between the cannula and the stylet to be engaged by the step as the stylet is being withdrawn from the cannula, said ring forming a seal to prevent liquid leakage out of said cannula, said ring being removable from the cannula by an increased pulling force on the stylet.

8. A cannula assembly, comprising:

an elongated tubular cannula body having a tip section adapted to be inserted within a vascular conduit; and a stylet slidably positioned within the body, said stylet including a stop on its outer periphery which slides within the interior of the body so that if the tip of the body is in a vascular conduit, the stop limits withdrawal of the stylet when engaging a structure in the end of the cannula;

wherein said structure includes an anti-backflow ring slideably positioned in the end of the body remote from the tip, with an outer portion of said ring engaging said body and an inner portion of said ring engaging said stylet, thereby forming a seal to prevent leakage out of said cannula and forming a temporary limit for said stop when said stylet is in the process of being withdrawn from the cannula, said anti-backflow ring adapted to be forced out of said body when said stylet is further withdrawn from said body after said stop engages said anti-backflow ring.

9. The cannula assembly of claim 8, wherein said stylet stop is spaced from the stylet tip and is spaced from said tip section when the stylet is fully inserted into the cannula body, whereby said stylet can be withdrawn to the point where the stop engages said ring a temporarily limiting withdrawal of the stylet, and including means at a location between the tip of the partially withdrawn stylet and the tip of the cannula for limiting fluid flow into the cannula, said stylet being adapted to be fully withdrawn from the cannula including forcing said ring out of the cannula body.

10. A method of making a connection to a vascular conduit, comprising:

inserting the tip of a cannula assembly into the conduit;

partially withdrawing from the cannula a stylet, while keeping a stop on the stylet exterior within the cannula; and blocking flow through the cannula at a location between the cannula tip and the tip of the partially withdrawn stylet.

11. The method of claim 10, including:

completely withdrawing the stylet from the cannula; and making connections to the end of the cannula before opening the cannula.

12. The method of claim 1, including:

limiting the partial withdrawing of the stylet by engaging the stop with a ring positioned in the end of the cannula; and removing said ring from the cannula by engagement with said stop when the stylet is completely withdrawn from the cannula.

* * * * *